US006890730B1

(12) United States Patent
Latterich et al.

(10) Patent No.: US 6,890,730 B1
(45) Date of Patent: May 10, 2005

(54) SEQUENCE AND METHOD FOR INCREASING PROTEIN EXPRESSION IN CELLULAR EXPRESSION SYSTEMS

(75) Inventors: Martin Latterich, San Diego, CA (US); Kendall Powell, San Diego, CA (US)

(73) Assignee: The Salk Institute, La Jolla, CA (US)

( * ) Notice: Subject to any disclaimer, the term of this patent is extended or adjusted under 35 U.S.C. 154(b) by 0 days.

(21) Appl. No.: 09/458,779

(22) Filed: Dec. 10, 1999

(51) Int. Cl.⁷ .......................... C12P 21/00; C07H 21/04
(52) U.S. Cl. ................ 435/69.1; 435/320.1; 435/254.2; 435/254.21; 536/23.1; 536/24.1; 530/350
(58) Field of Search ............................ 435/69.1, 320.1, 435/254.2, 254.21; 536/23.1, 24.1; 530/350

(56) References Cited

U.S. PATENT DOCUMENTS

| | | | | |
|---|---|---|---|---|
| 4,775,622 | A | 10/1988 | Hitzeman et al. | .......... 435/69.4 |
| 5,436,136 | A | 7/1995 | Hinnen et al. | .............. 435/69.1 |
| 5,672,487 | A | 9/1997 | Schweden et al. | .......... 435/69.1 |
| 5,834,262 | A | 11/1998 | Anton et al. | ................. 435/136 |

OTHER PUBLICATIONS

Livingstone–Zatchej et al. Nuc. Acid Res. 25: 3795–3800, 1997.*
Everett et al..Nature Genetics 17: 411–422, 1997.*
Scott et al. Nature Genetics 21: 440–443, 1999.*
Johnston et al. Cloning and characterization of the *Schizosaccharomyces pombe* DNA ligase gene CDC17. 1986. Gene 41:321–325.*
Pagan–Ramos et al. Replacement of the *Saccharomyces cerevisiae* RPR1 gene with heterologous RNase P RNA genes. Jan. 25, 1994. Nuc. Acids. Res. 22:200–207.*
Madison et al. Identification and analysis of homologues of *Saccharomyces cerevisiae* Spt3 suggest conserved functional domains. Mar. 30, 1998. Yeast 14:409–417.*
Mukai et al. Conservation of histone binding and transcriptional repressor functions in a *Schizosaccharomyces pombe* Tup1p homolog. Dec. 1999. Mol. Cell. Biol. 19:8461–8468.*
Romanos et al., Yeast 8: 423–488, Foreign gene expression in yeast: a review, 1992.*
Zhou et al. Identification of a novel high affinity copper transport complex in the fusion yeast *Schizosaccharomyces pombe*. Jun. 8, 2001. Journal of Biological Chemistry. 276:20529–20535.*
EMBL entry EMBL:SCL9476.*
Mannhaupt, et al. Characterization of the prephenate dehydrogenase–encoding gene, TYR1, from *Saccharomyces cerevisiae*. Dec. 28, 1989. Gene 85(2): 303–311.*
Powell et al. Molecular Biology of the Cell 10(supplement):298a, abstract No. 1727, Nov. 1999.*

Brake, A.J., et al., "α–factor–directed synthesis and secretion of mature foreign proteins in *Saccharomyces cerevisiae*", *PNAS, 81*, pp. 4642–4646, (Aug. 1984).
Eakle, K.A., et al., "Characterization of a Component of the Yeast Secretion Machinery: Identification of the SEC18 Gene Product", *Molecular and Cellular Biology, 8 (10)*, pp. 4098–4109, (Oct. 1988).
Fernandez–Lafuente, R., et al., "Chemoenzymatic One–pot Synthesis of Cefazolin Cephalosporin C in Fully Aqueous Medium, Involving Three Consecutive Biotransformations Catalyzed by D–Aminoacid Oxidase, Glutaryl Acylase and Penicillin G Acylase", *Tetrahedron Letters, 38 (26)*, pp. 4693–4696, (1997).
Gavagan, J.E., et al., "Chemoenzymic Synthesis of N–(Phosphonomethyl) glycine", *J. Org. Chem., 62 (16)*, pp. 5419–5427, (Aug. 1997).
Griff, I.C., et al., "The Yeast SEC17 Gene Product Is Functionally Equivalent to Mammalian α–SNAP Protein", *The Journal of Biological Chemistry, 267 (17)*, pp. 12106–12115, (Jun. 15, 1992).
Lehninger, A.L., "Chapter 4: The Amino Acid Building Blocks of Proteins", *Biochemistry, Second Edition*, Worth Publishers, Inc., pp. 73–75, (1975).
Morin–Ganet, M.N., et al., "Role of Endoplasmic Reticulum–Drived Vesicles in the Formation of Golgi Elements in sec23 and sec18 *Saccharomyces Cerevisiae* Mutants", *The Anatomical Record, 251 (2)*, pp. 256–264, (1998).
Patel, S., et al., "The AAA Team: Related ATPases With Diverse Functions", *Trends in Cell Biology, 8*, pp. 65–71, (Feb. 1998).
Powell, K.S., et al., "Vff2p, a nuclear sec17/sec18 suppressor in vesicular traffic and fusion", *Mol. Biol. Cell, 10 Suppl., Membrane Fusion Abstracts,* Abstract No. 1727, p. 298a, (Nov. 1999).
Pryer, N.K., et al., "Vesicle–Mediated Protein Sorting", *Annu. Rev. Biochem., 61,* pp. 471–516, (1992).
Sakaguchi, M., "Eukaryotic Protein Secretion", *Current Opinion in Biotechnology, 8,* pp. 595–601, (1997).
Schweizer, F.E., et al., "Regulation of Neurotransmitter Release Kinetics by NSF", *Science, 279,* pp. 1203–1206, (Feb. 1998).

(Continued)

Primary Examiner—James Ketter
Assistant Examiner—David Lambertson
(74) Attorney, Agent, or Firm—McDermott Will & Emery LLP

(57) ABSTRACT

The invention provides a novel protein that, when expressed in a host cell, increases cellular biomass and cellular protein production and secretion. The invention also provides a polynucleotide encoding the novel protein, and methods for using the polynucleotide and encoded protein to increase cellular biomass and cellular protein production and secretion. Also provided is a genetically altered mutant cell strain with enhanced production and secretion of cellular and heterologous proteins.

44 Claims, 3 Drawing Sheets

OTHER PUBLICATIONS

Segev, N., et al., "The Yeast GTP–Binding YPT1 Protein and a Mammalian Counterpart Are Associated with the Secretion Machinery", *Cell, 52,* pp. 915–924, (Mar. 1988).

Shaulsky, G., et al., "Development signal transduction pathways uncovered by genetic suppressors", *PNAS, 93,* pp. 15260–15265, (Dec. 1996).

Steel, G.J., et al., "Biochemical Analysis of the *Saccharomyces cerevisiae* SEC18 Gene Product: Implications for the Molecular Mechanism of Membrane Fusion", *Biochemistry, 38,* pp. 7764–7772, (1999).

Stryer, L., "Introduction to Protein Structure and Function", *Biochemistry, Second Edition,* Chapter 2, W.H. Freeman and Company, San Francisco, CA, pp. 14–15, (1981).

Tanaka, K., et al., "Characterization of a Fission Yeast SUMO–1 Homologue, Pmt3p, Required for Multiple Nuclear Events, Including the Control of Telomere Length and Chromosome Segregration", *Molecular and Cellular Biology, 19* (*12*), pp. 8660–8672, (Dec. 1999).

Witt, W., et al., "Secretion of Phospholipase B From *Saccharomyces Cerevisiae*", *Biochimica et Biophysica Acta, 795,* pp. 117–124, (1984).

Woodman, P.G., et al., "Functional Conservation of Cytosolic Proteins Required for Endosomal Vesicle Fusion", *Yeast, 12,* pp. 1251–1262, (1996).

Zsebo, K.M., et al., "Protein Secretion from *Saccharomyces cerevisiae* Directed by the Prepro–α–factor Leader Region", *The Journal of Biological Chemistry, 261* (*13*), pp. 5858–5865, (May 5, 1986).

"AFG1 Protein—Yeast (*Saccharomyces Cerevisiae*)", *NCBI Protein S30825.*

"agCP10084 [Anopheles Gambiae Str. PEST]", *EAA07345.*

"Alpha–soluble NSF Attachment Protein [*Arabidopsis Thaliana*]", *NCBI Protein NP 191178.*

"Alpha–soluble NSF Attachment Protein–like [*Arabidopsis thaliana*]", *NCBI Protein—NP 191204.*

"ATPase", *NCBI Protein AAA34414.*

"BLASTP 2.2.3 [Apr. 24, 2002]".

"BLASTP 2.2.4 [Aug. 26, 2002]".

"BRCA2 and CDKN1A–Interacting Protein Isoform BCCIPalpha; BRCA2 and CDKN1A–interacting Protein; cdk Inhibitor p21 binding protein; BCCIPalpha; BCCIPbeta; TOK–1alpha; TOK–1beta [Homo Sapiens]", *NCBI Protein—NP 057651.*

"Hypothetical ORF; Bcp1p [*Saccharomyces Cerevisiae*]", *NCBI Protein—NP 010648.*

"Hypothetical Protein [*Schizosaccharomyces Pombe*]", *NCBI Protein—NP 587696.*

"Hypothetical Protein [*Schizosaccharomyces Pombe*]", *NCBI Protein—CAA21060.*

"Nsf; N–ethylmaleimide Sensitive Factor [*Rattus Norvegicus*]", *NCBI Protein—NP 068516.*

"SEC18 Protein—Yeast (*Saccharomyces Cerevisiae*)", *NCBI Protein S45477.*

"Unknown", *NCBI Protein AAB60280.*

"Vesicular–fusion protein NSF (N–ethylmameimide–sensitive fusion protein) (NEM–sensitive fusion protein)", *NCBI Protein P46459.*

"Vesicular–fusion Protein NSF [*Caenorhabditis Elegans*]", *NCBI Protein NP 492152.*

"Vesicular–fusion Protein Nsf1 (N–ethylmaleimide–sensitive Fusion Protein 1) (NEM–sensitive Fusion Protein 1) (DNsf–1) (Comatose Protein)", *NCBI Protein—P46461.*

"Vesicular–fusion Protein Nsf2 (N–ethylmaleimide–sensitive Fusion Protein 2) NEM–sensitive Fusion Protein 2) (DNsf–2)", *NCBI Protein—P54351.*

"Vesicular–fusion Protein SEC18", *NCBI Protein P34732.*

"Vesicular–fusion Protein Sec18.", *NCBI Protein P18759.*

* cited by examiner

A

| GAL 1/10 | Signal peptide | Protein X | GAL 1/10 | VFF2 | | ars | amp' | neo | ars |

B

| GAL 1/10 | VVF2 | | amp' | neo | ars | ori |

| GAL 1/10 | Signal peptide | Protein X | | amp' | zeo | ars | ori |

| | | | |
|---|---|---|---|
| GAL 1/10 | = | Galactose inducible promoter | |
| ori | = | Origin of replication | |
| neo | = | Geneticin resistance | |
| ars | = | autonomous replicating sequence | |
| ampr | = | Ampicillin resistance | |
| vvf2 | = | vesicular fusion factor 2 gene | |
| zeo | = | zeocin resistance gene | |
| Protein "X" | = | Protein to be expressed | |

FIGURE 1

Growth at 24 °C

Growth at 37 °C

SEQUENCE LISTING

```
<160> NUMBER OF SEQ ID NOS: 2

<210> SEQ ID NO 1
<211> LENGTH: 852
<212> TYPE: DNA
<213> ORGANISM: Saccharomyces cerevisiae

<400> SEQUENCE: 1
atggttcaag ctatcaaatt aaatgattta aaaaatagga agagaaaaaa tgtggaggaa      60
gaaaatggca gtgacgagtc tgaaattgac attagtagca ccgattcaga aaatgaagaa     120
gagcaaaatg gagaagaaga gatcgtaaat attgacttcg atttttttcgg tggtaaccca    180
```

-continued

```
gaagttgatt ttcatgcttt aaagaattta ctgcgtcagt tatttggtcc tcaagaaagt      240
accaggattc aactaagcag cttggcagat ttgatcctag gttccccaac caccacaatt      300
aaaacagacg gcaaagaatc tgatccatac tgttttcttt cattcgttga tttcaaagct      360
aatcatctaa gtgattatgt caaatattta caaaaagtgg acatgagact ttccactttc      420
ttcaaaacta tgattgatag tggtaataaa aattgtgctt tggttctcag tgaaaggctg      480
attaatatgc caccggaagt cgttccacct ttatacaaga ttcgttgga ggatgttgcc       540 acggcacttg gcgatgacaa acattatgac ttctatatca tcgtcaccag gaagtatgaa      600
gtaaattttg acactgacga tgataccgac tctggtaaga ggaataaaaa caaagacgaa      660
agatccaaaa aaagggtgaa ggccgatgaa gtagactact ttcatgagga ggaccgattt      720
tttgaaaaat atgccaagat tcacttcgaa tcagaagcta aaaagggtgt tatcagctca      780
tacatgattc ttgatcacga aggccttgtc aaaagtatcg atgaattgga aacagaaatt      840
tccacttggt aa                                                         852

<210> SEQ ID NO 2
<211> LENGTH: 283
<212> TYPE: PRT
<213> ORGANISM: Saccharomyces cerevisiae

<400> SEQUENCE: 2

Met Val Gln Ala Ile Lys Leu Asn Asp Leu Lys Asn Arg Lys Arg Lys
 1               5                  10                  15

Asn Val Glu Glu Glu Asn Gly Ser Asp Glu Ser Glu Ile Asp Ile Ser
            20                  25                  30

Ser Thr Asp Ser Glu Asn Glu Glu Gln Asn Gly Glu Glu Glu Ile
        35                  40                  45

Val Asn Ile Asp Phe Asp Phe Phe Gly Gly Asn Pro Glu Val Asp Phe
    50                  55                  60

His Ala Leu Lys Asn Leu Leu Arg Gln Leu Phe Gly Pro Gln Glu Ser
65                  70                  75                  80

Thr Arg Ile Gln Leu Ser Ser Leu Ala Asp Leu Ile Leu Gly Ser Pro
                85                  90                  95

Thr Thr Thr Ile Lys Thr Asp Gly Lys Glu Ser Asp Pro Tyr Cys Phe
            100                 105                 110

Leu Ser Phe Val Asp Phe Lys Ala Asn His Leu Ser Asp Tyr Val Lys
        115                 120                 125

Tyr Leu Gln Lys Val Asp Met Arg Leu Ser Thr Phe Phe Lys Thr Met
    130                 135                 140

Ile Asp Ser Gly Asn Lys Asn Cys Ala Leu Val Leu Ser Glu Arg Leu
145                 150                 155                 160

Ile Asn Met Pro Pro Glu Val Pro Pro Leu Tyr Lys Ile Thr Leu
                165                 170                 175

Glu Asp Val Ala Thr Ala Leu Gly Asp Asp Lys His Tyr Asp Phe Tyr
            180                 185                 190

Ile Ile Val Thr Arg Lys Tyr Glu Val Asn Phe Asp Thr Asp Asp
        195                 200                 205

Thr Asp Ser Gly Lys Arg Asn Lys Asn Lys Asp Glu Arg Ser Lys Lys
    210                 215                 220

Arg Val Lys Ala Asp Glu Val Asp Tyr Phe His Glu Glu Asp Arg Phe
225                 230                 235                 240

Phe Glu Lys Tyr Ala Lys Ile His Phe Glu Ser Glu Ala Lys Lys Gly
                245                 250                 255
```

```
Val Ile Ser Ser Tyr Met Ile Leu Asp His Glu Gly Leu Val Lys Ser
            260                 265                 270

Ile Asp Glu Leu Glu Thr Glu Ile Ser Thr Trp
            275                 280
```

SEQUENCE AND METHOD FOR INCREASING PROTEIN EXPRESSION IN CELLULAR EXPRESSION SYSTEMS

BACKGROUND OF THE INVENTION

Proteins are needed for a variety of uses, especially for commercial food and chemical production and for medically therapeutic uses. These proteins may not be readily isolated from their natural sources, or may be needed in a mutated, or non-naturally occurring form. In such cases expression of heterologous proteins from cellular expression systems has proven useful.

Cellular expression systems rely on host cells, such as bacterial, yeast, fungal, and mammalian cells for expression of heterologous proteins. Bacterial cells provide an advantage in terms of ease of cultivation on inexpensive growth media and ease of manipulation of heterologous gene expression vectors. Heterologous proteins produced in bacterial expression systems can be isolated from inclusion bodies produced within the bacteria. They can also be isolated from the periplasmic space if the heterologous protein has been expressed in conjunction with a signal recognition sequence, or leader sequence, that directs the protein through the bacterial secretory pathway. Bacterial systems have been found to be disadvantageous, however, for expression of certain eukaryotic proteins, because they do not provide the intracellular machinery for appropriate post-translational modification of the proteins. Bacterial expression systems are also not the system of choice in many instances because some bacterial products, such as the bacterial lipopolysaccharide (LPS), are toxic to humans.

Mammalian expression cell systems produce appropriately modified proteins. They are not the systems of choice for producing many proteins, though, because they generally require the use of immortalized cell lines that also include proteins that transform cells, and because they are more expensive to maintain.

Yeast expression systems provide the same ease of cultivation on inexpensive growth media as do bacteria. They also provide the same ease of manipulation of heterologous expression vectors. They are advantageous over bacterial expression systems because they allow expression of proteins with appropriate post-translational modifications, such as proteolytic processing, folding, disulfide bridge formation, and glycosylation. Yeasts have also proven to be safe for human consumption through years of use in food and beverage production. Yeasts have also been used for large-scale production of human, animal, viral, and plant proteins since the early 1980s. Several species of yeast have been used to produce these foreign proteins, including *Saccharomyces cerevisiae, Schizosaccharomyces pombe, Pichia pastoris, Hansenula polymorpha, Kluyveromyces lactis,* and *Yarrowia lipolytica*.

*Saccharomyces cerevisiae*, with its long history of use in the production of bread and alcoholic beverages, is considered a safe organism for human consumption and has been more thoroughly characterized than any other species. It has therefore been the species of choice for many expression systems. A transmembrane receptor, rat somatostatin receptor type 2, as well as a surface protein, Pfs25 of *Plasmodium falciparum*, are examples of a large number of proteins that have been expressed in a *Saccharomyces* expression system.

Both intracellular and extracellular yeast expression systems have been used for heterologous protein production. Intracellular expression is preferred for proteins that are expressed in the cytoplasm, or for secreted proteins with few or no disulfide bonds. Extracellular expression, or secretion of heterologous proteins into the culture medium, provides the advantage of avoiding toxicity caused by accumulated protein and also allows for simple purification procedures. Passage of the heterologous protein through the secretory pathway also allows the heterologous protein to be post-translationally modified.

In yeast and higher eukaryotic cells Sec18p and NSF, respectively, can interact with SNARE proteins to stimulate secretory traffic in the cell. In yeast, Sec18p works in conjunction with Sec17p to promote protein secretion through sequential membrane vesicle fusion, while in mammalian cells the Sec18p counterpart, N-ethylmaleimide-sensitive factor (NSF), works in conjunction with the Sec17p mammalian counterpart, alpha-SNAP, to accomplish the same result. The secretory pathways of the two systems are remarkably similar, as indicated by the sequence identity between the proteins associated with each system and the fact that the yeast and mammalian proteins are, to a great extent, interchangeable.

Sec18p has 67% sequence identity with squid NSF, and squid NSF has approximately 75% homology with NSF found in Chinese hamster ovary cells (CHO-NSF) and *Drosophila* NSF (d-SNF1). Schweizer, et al., *Science* (1998) 279: 1203. Furthermore, when Sec18p is introduced into mammalian cells, it has been shown to interact with synaptic SNARE proteins and to synergize with alpha-SNAP to stimulate exocytosis in those cells, demonstrating that the proteins associated with membrane fusion and protein secretion are conserved from yeast to mammals. Steel, G. J., et al., *Biochemistry* (1999) 38(24): 7764.

The yeast Sec17 gene product has been shown to be functionally equivalent to the alpha-SNAP protein, exhibiting the exact biochemical properties expected for a yeast homolog of the mammalian transport factor. Griff, I. C., *J. Biol. Chem* (1992) 267: 12106. Yeast cytosol can support mammalian endosomal vesicle fusion, demonstrating that there is conservation between yeast and mammalian cells in terms of cytosolic components required for vesicle fusion. Woodman, P. G., *Yeast* (1996) 12: 1251.

Unfortunately, production of proteins in *S. cerevisiae*, either intracellularly or through the secretory pathway, results in a limited yield. In cytoplasmic expression systems, this problem has been addressed by fusing the target protein to a stable protein such as human superoxide dismutase (SOD) or human gamma interferon (IFNγ). A ubiquitin fusion expression system has also been used to increase yield and protein stability.

For secreted proteins, yield has been increased by using methylotrophic yeast, such as *Pichia pastoris* or *Hansenula polymorpha*, as host cells. Although these species have been shown to produce increased amounts of some proteins, particularly human serum albumin (which is secreted at 4 g/l by *P. pastoris*), protein secretion still does not regularly occur at a level that makes any of the yeast species efficient sources for heterologous protein production. Furthermore, expression in methylotrophic yeast requires the use of methanol, a highly volatile substance, in the culture environment.

In some cases, overexpression of certain proteins in conjunction with the target heterologous protein has been effective for increasing target protein secretion. Human leukocyte protease inhibitor, for example, has been shown to be secreted at a three- to four-fold higher rate when ubiquitin was simultaneously overexpressed from a chromosomal UB14 gene under the control of the GAL1 promoter. Nevertheless, those of skill in the art continue to search for host cells, expression vectors, and methods for increasing protein production and secretion in cellular expression systems.

Therefore, there is a continuing need for improved cellular expression systems that produce higher yields of heterologous proteins and can be subjected to relatively easy production and purification techniques.

SUMMARY OF THE INVENTION

The invention provides a polynucleotide encoding a functional vesicular fusion factor 2 protein (hereinafter the "VFF2 nucleotide sequence" and "Vff2 protein" or "Vff2p", respectively), or a structural or functional homolog of Vff2p. A "structural or functional homolog," as used herein, is a sequence that is conserved between nucleotide or amino acid sequences, or is a protein that has a conserved structure or function in a cell. In one embodiment, the VFF2 nucleotide sequence is isolated and may also be free of introns. The VFF2 nucleotide sequence may be SEQ ID NO:1. The Vff2p sequence may be SEQ ID NO:2. The isolated polynucleotide may be positioned so as to be expressed under the control of a polynucleotide promoter sequence appropriate in a host cell. Also provided are variants of the VFF2 nucleotide sequence, such as functionally equivalent insertion, deletion and substitution sequences. These insertions and/or deletions may be made to non-essential regions of the VFF2 sequence. The substitutions may be conserved substitutions. The polynucleotide may also contain a sequence encoding a target protein that is operably linked to a second promoter.

Also provided is a polynucleotide expression vector containing SEQ ID NO:1 and related elements necessary for cellular expression of the protein encoded by SEQ ID NO:1. For example, a promoter sequence that directs transcription of SEQ ID NO:1 in a host cell can be incorporated into the polynucleotide expression vector.

Also provided is the Vff2 protein. This protein may be SEQ ID NO:2. The Vff2 protein can be about 32 kD in size.

The invention also provides a recombinant host cell that is a cell genetically altered to express the Vff2 protein. The host cell may be a yeast cell. The yeast cell can be a *Saccharomyces cerevisiae, Schizosaccharomyces pombe, Yarrowia lipolytica, Pichia pastoris, Hansenula polymorpha,* or *Kluyveromyces lactis* cell. Specifically, the invention provides a yeast secretory mutant that has been genetically altered by transformation with the VFF2 polynucleotide sequence to secrete enhanced amounts of one or more proteins produced by the cell.

Furthermore, the invention provides a method for increasing protein production or secretion from a cell. The method involves the steps of introducing the polynucleotide encoding VFF2 into a host cell and culturing the host cell under conditions effective to allow expression of the encoded VFF2 polynucleotide sequence.

The invention also provides a method of selecting for a yeast secretory mutant cell containing a VFF2 nucleotide sequence by growing the recombinant cell at a temperature of about 32–37° C. The secretory mutant cell can be sec17-1, sec18-1, bet1-1, sec22-2, uso1-1, pex3-1, sed5-l, cdc48-2, sec7-5, or ypt1-3.28. Specifically it can be sec17-1, sec18-1, bet1-1, sec22-2, uso1-1, or pex3-1, and in particular sec18-1.

BRIEF DESCRIPTION OF THE DRAWINGS

FIGS. 1A and 1B. These are schematics of possible vectors that can be made in accordance with the present invention. FIG. 1A depicts a single vector containing both VFF2 and a gene for a target protein "X". FIG. 1B depicts a combination of two vectors where the first vector has the VFF2 gene, and the second vector has the gene for a target protein "X".

FIG. 3A shows growth at 24° C. and FIG. 3B shows growth at 37° C.

DETAILED DESCRIPTION OF THE INVENTION

Figure 2:
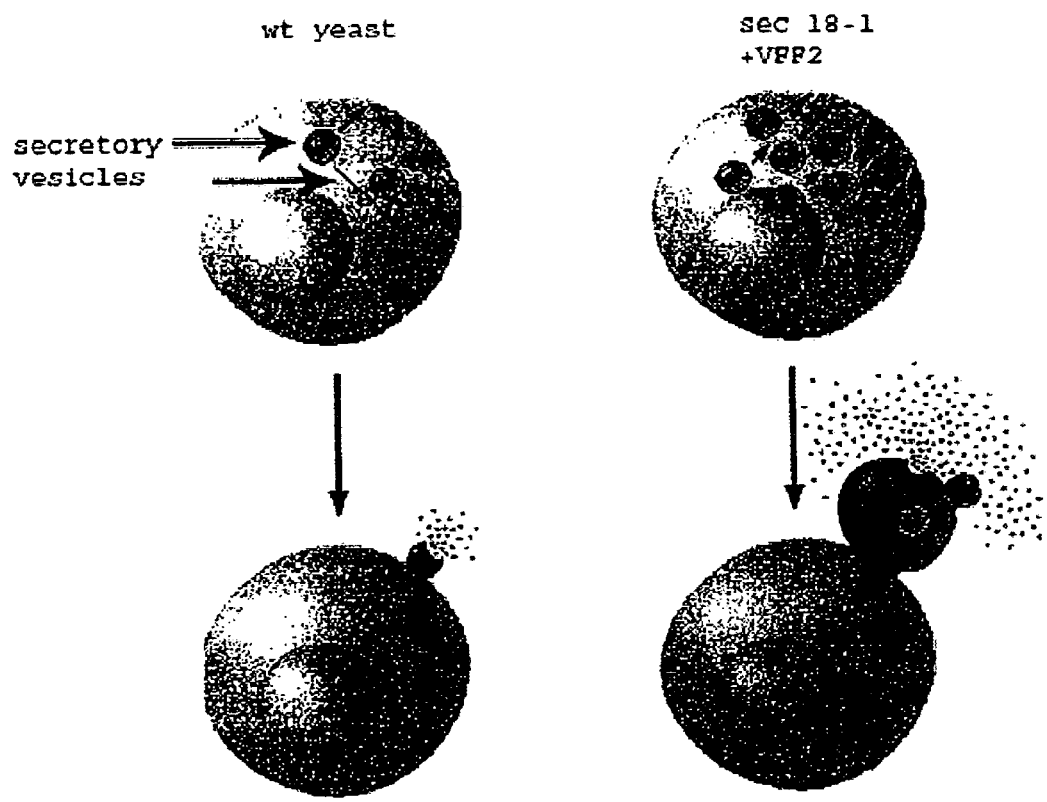
FIG. 2. This is a schematic drawing of how VFF2 promotes growth of the sec18-1 strain and how this is tied to increased secretion.

Cell growth and division is a tightly regulated process. The yeast cell synthesizes, in a concerted fashion, proteins and lipids to allow for an expansion of the cellular perimeter, ultimately resulting in the generation of a daughter cell. The secretion of lipids and proteins is needed to allow for cellular growth, because the plasma membrane needs to increase in surface area. If sufficient nutrients are available, the cell selects a site on its plasma membrane to generate and grow a bud, representing the daughter cell. Vectorial secretion of proteins and lipid membranes ensures further growth of the bud, until the bud has reached the size of the original mother cell, and intracellular organelles have been partitioned. The two cells will separate by septation, and a new cycle of cell growth and division occurs. Cell growth is dependent on the secretion of vesicles and their cargo. For secretion to occur, vesicles have to fuse with organelles and ultimately the plasma membrane. This fusion process requires numerous secretory proteins, such as, but not limited to, Sec17p, Sec18p, SNAREs and other proteins, that confer specificity of fusion and are participants in the fusion mechanism. Cellular growth is commonly rate limited by availability of nutrients, cell cycle checkpoints and secretion. A common aim is to metabolically engineer production strains of yeast to enhance levels of secretion and protein production. This can be achieved by identifying the rate limiting steps of key metabolic and cellular pathways, and improving these bottlenecks. Unfortunately, it is not clear what limits the rate of secretion, limiting strategic improvement of secretion.

The present invention provides a protein, a polynucleotide sequence encoding the protein, and a method of using the protein to increase intracellular production or secretion of a heterologous protein in a cellular expression system, including yeast and higher eukaryotic cell expression systems. In particular, a novel protein, vesicular fusion factor 2 or "Vff2p", and its corresponding novel polynucleotide sequence, VFF2, have been discovered and isolated. In addition, a method for using VFF2 and Vff2p to increase intracellular protein or secreted protein in a cellular expression system has been discovered.

Proteins acting in a biochemical pathway, such as Vff2p, can be identified by means of a genetic suppression screen. Briefly, a genetic suppression screen identifies mutations for which the phenotype can be overcome by expression of or addition of a target protein. If the target protein is unknown, it can be identified by its presence in those cells in which the known mutation has been suppressed. According to the present invention, an overexpression suppressor screen has been developed and has enabled the discovery of the Vff2 protein as a suppressor of mutations in, for example, v-SNARE proteins, t-SNARE proteins, Sec18p, Sec17p, and Ypt1p (a small rab-like GTPase required for initial tethering of vesicles). Eakle, K. A., et al., *Mol. Cell Biol.* (1988) 16

(15): 7499; Griff, I. C., et al., *J Biol. Chem.* (1992) 267 (17): 12106; Pryer, N. K., et al., *Annu. Rev. Biochem.* (1992) 61: 471; Segev, N., et al., *Cell* (1988) 52 (6): 915. Overexpression of the Vff2 protein in such secretory mutants has been discovered to result in at least a two-fold increase in the rate of protein secretion and the cellular biomass.

Three different groups of secretory mutations have been identified: 1) mutations that are strongly suppressed by VFF2, 2) mutations that are suppressed by VFF2 but not as strongly, and 3) mutations that are not suppressed by VFF2. Examples of mutations that fall into the first group are sec17-1, sec18-1, bet 1-, sec22-2, uso1-1, pex3-1. With the exception of pex3-1, these mutations can generally be described as mutations in proteins, which are involved early in the secretory pathway and/or involved in the required cellular machinery for membrane fusion. These strains would most likely be usable for selection using high temperature.

Examples of mutations that fall into the second group are sed5-1, cdc48-2, sec7-5, ypt1-3. These mutations are also in the early secretory pathway but are less useful in high temperature selection.

Examples of mutations that fall into the last group are ufe1-1, tip20-5, sec20-5, sec18-1sec23-1 (double mutant), sec21-4, vps6, vam3. These mutations are not suppressed by VFF2. One thing they have in common is that they are all involved in a step of the secretory pathway that is not part of the secretory apparatus. In other words, these mutations are not in the linear secretory pathway, as are the group 1 and 2 mutations. Instead, they are in branched pathways not directly involved in the secretion process.

A polynucleotide sequence of the present invention is a sequence encoding a functional Vff2 protein. It is well known that one or more nucleotide substitutions can be made to a polynucleotide sequence without affecting production of a functional protein. For example, the third nucleotide position of a codon at times may be changed without changing the amino acid encoded by that codon. In some cases, the first and second positions may also be changed without effecting a change in the amino acid encoded by the codon. It is also known that additional nucleotides can be added either 5N or 3N, or both, to a polynucleotide sequence without affecting expression of a functional protein from that polynucleotide. In fact, it is often desirable to place nucleotides encoding transcriptional or translational elements at positions 5N or 3N to a polynucleotide protein-coding region in order to increase or regulate protein expression. It is also desirable to incorporate the protein-coding polynucleotide sequence into an appropriate plasmid or other expression vector in order to effect expression of the desired target protein. Therefore, the present invention includes modifications of a polynucleotide sequence of SEQ ID NO:1, wherein that sequence has been modified by any of the changes previously discussed, has been modified internally, or wherein that sequence or modification thereof has been linked to added 5N or 3N nucleotides without changing the functionality of the protein expressed therefrom.

A protein sequence of the present invention is an amino acid sequence for a native Vff2p or variant thereof. A "variant" of Vff2p is a polypeptide that is not completely identical to native Vff2p. Such a variant Vff2p can be obtained by altering the amino acid sequence by insertion, deletion or substitution of one or more amino acids. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. For the purpose of the conserved substitution, the 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains. See, for example, L. Stryer, *Biochemistry* (2d ed.) p. 14–15; Lehninger, *Biochemistry*, p. 73–75.

The amino acid changes are achieved by changing the codons of the corresponding nucleic acid sequence. It is known that such polypeptides can be obtained based on substituting certain amino acids for other amino acids in the polypeptide structure in order to modify or improve secretory activity or cellular growth or division. For example, through substitution of alternative amino acids, small conformational changes may be conferred upon a polypeptide that result in increased activity. Alternatively, amino acid substitutions in certain polypeptides may be used to provide residues that may then be linked to other molecules to provide peptide-molecule conjugates that retain sufficient secretory properties of the starting polypeptide to be useful for other purposes.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made on the basis of hydrophilicity. Accordingly, it is noted that substitutions can be made based on the hydrophilicity assigned to each amino acid.

In using either the hydrophilicity index or hydropathic index, which assigns values to each amino acid, it is preferred to conduct substitutions of amino acids where these values are ±2, with ±1 being particularly preferred, and those with in ±0.5 being the most preferred substitutions.

A variant of the invention may include amino acid residues not present in the corresponding native Vff2p or deletions relative to the corresponding native Vff2p. A variant may also be a "fragment" as compared to the corresponding native Vff2p, ie., only a portion of a fulllength protein. "Recombinant" is defined as a peptide or nucleic acid produced by the processes of genetic engineering. The terms "protein," "peptide" and "polypeptide" are used interchangeably herein.

According to the present invention, Vff2p of SEQ ID NO:2 is a yeast protein sequence. This protein is useful for increasing cell mass and secretion of expressed proteins in yeast. Analyses of various databases have indicated that SEQ ID NO:1 and SEQ ID NO:2 are unique sequences in the yeast *S. cerevisiae*. By doing a BLAST analysis, homologous sequences have been identified in *S. pombe*, the nematode *Caenorhabditis elegans*, and the plant *Arabidopsis*. These homologous regions are simply open reading frames (ORFs) in the sequenced genome of these organisms. These ORFs have not been studied to date. Vff2p had 36% identity (i.e., identical amino acids) and 56% homology (i.e., the amino acids were of the same structure/function group, as described above) with *S. pombe*; had 25% identity and 46% homology with *Arabidopsis*; and 24% identity and 40% homology with *C. elegans*. It is quite surprising that there would be a high level of identity and homology in such diverse organisms.

As mentioned previously, however, proteins of the cellular secretory pathway are conserved between a number of unlike species. Therefore, according to the invention, a nucleotide sequence of SEQ ID NO:1, is used to increase secretion in other eukaryotic cell expression systems, as well as used as a probe to identify proteins of the same function in other cell types. The method of the present invention can therefore be utilized in a variety of cell types, including plant and animal cell expression systems, to increase protein production and secretion.

In the method of the present invention, the Vff2 protein is used to increase heterologous protein production and secretion in yeast cells. In other types of cells, Vff2p or Vff2 protein homologs can be used to increase production and/or secretion of heterologous proteins.

Vff2p may be introduced into a host cell by transformation of the host cell with a polynucleotide encoding the Vff2 protein, such as SEQ ID NO:1. Briefly, the polynucleotide can be incorporated into a suitable expression vector using methods known to those of skill in the art. Examples of yeast cloning and expression vectors include, for example, yeast integrative plasmids (YIps), consisting of bacterial plasmids with an added marker for selection in yeast. These vectors require integration into the yeast genome for stable inheritance, since they contain no yeast origin of replication.

Yeast replicating plasmids (YRps) contain an origin of replication derived from the yeast chromosome. The plasmids can replicate without being integrated into the chromosome. One should keep in mind, however, that since yeast reproduce by budding, YRps are frequently lost in the offspring and therefore require the use of suitable selection techniques.

Yeast centromeric plasmids (YCps) can be used where a low copy number is desired, such as where a protein will accumulate to toxic levels within the cell before being secreted. The centromeric sequence incorporated into the YCp allows it to function like a chromosome during cell division. The YCp is therefore distributed to daughter cells of each generation and is more stable without maintenance by selection.

Yeast artificial chromosomes (YACs) provide an advantage, according to the invention, particularly where Vff2p is expressed in conjunction with a target heterologous protein from the same expression vector, because there is relatively no limit to the amount of foreign DNA that can be cloned into a YAC. Since the YAC contains an autonomously replicating sequence, a centromeric sequence, and a telomere at each end, it can be consistently transmitted to daughter cells.

A vector that allows for high-level expression of the VFF2 polynucleotide sequence is a yeast expression plasmid (YEp), which contains the origin of the endogenous, autonomously replicating high-copy-number 2 micron plasmid. YEps, though poorly segregated into daughter cells, are stably maintained because of their high copy number. When the entire 2 micron plasmid DNA is inserted into yeast cells lacking an endogenous plasmid, copy numbers in excess of 200 per cell can be achieved.

The Vff2 protein (SEQ ID NO:2) of the present invention can be expressed from the VFF2 polynucleotide sequence (SEQ ID NO:1) under the control of any one of a variety of suitable promoters. Many suitable promoters are described in the prior art. The promoter may be a constitutive promoter, or may be an inducible promoter. For example, a constitutive promoter may be used when a constant high level of expression is desired. Alternatively, a temperature-sensitive promoter may be used. Regulatable promoters used in yeast expression systems include, for example, the upstream sequence for the alcohol dehydrogenase gene (ADH2) and the triose phosphate dehydrogenase gene, as well as GAL1, GAL7, or GAL10 in conjunction with GAL4, regulated by galactose. Suitable promoters also include the PHO5 acid phosphatase and CUP1, which codes for metallothionine and is induced by $Cu^{2+}$ or $Zn^{2+}$. In methylotrophic yeast, such as *Pichia pastoris* and *Hansenula polymorpha*, the AOX1 or related promoters provide tight repression of transcription by glucose and most other carbon sources, and induction to levels of greater than 1000× in cells shifted to methanol as the sole carbon source. An effective promoter in *S. cerevisiae* is the inducible GAL1/10 promoter, which can be induced to direct transcription of the VFF2 polynucleotide sequence when host cells are streaked onto plates containing YPGa1 medium.

Transformation of yeast cells with an expression vector containing the VFF2 polynucleotide sequence can be accomplished by methods known to those of skill in the art. Briefly, yeast cell walls can be removed by enzyme digestion, and the resulting spheroplasts can be incubated with vector DNA in the presence of calcium and polyethyleneglycol. Alternatively, intact yeast cells can be treated with alkali metal ions, such as $Li^+$, and then incubated with the vector DNA in the presence of polyethyleneglycol. A third method for transforming yeast cells is electroporation, a technique that has been described in the literature and is well known to those of skill in the art.

Selection procedures for maintaining foreign genetic elements in yeast are commonly designed to utilize a yeast host strain that is defective in the biosynthesis of one or more amino acids, purines, or pyrimidines, in conjunction with a vector for the foreign DNA that contains a yeast gene for the missing function. Examples of nutritional selection markers in yeast expression systems include the LEU2 gene (which supports leucine biosynthesis), the URA3 gene (which supports uracil biosynthesis), and the HIS3 gene (which supports histidine biosynthesis). Cells deficient in any of the genes needed for biosynthesis of nutritional molecules cannot be grown on minimal medium. Therefore, cells that have successfully incorporated the marker DNA can be selected on the basis of their ability to survive and grow on minimal media. This is particularly useful to inhibit the proliferation of undesired yeast strains.

In the method of the present invention, the VFF2 polynucleotide sequence is transferred to a yeast secretory mutant, such as, for example, sec18-1 or sec17-1. Yeast secretory mutants are functionally defective in one or more of the proteins involved in the yeast secretory pathway. A good secretory mutant for use in the method of the present invention is sec18-1.

A target protein may also be introduced into the host cell, by methods previously described. The target protein can be introduced into the host cell in conjunction with the VFF2 polynucleotide sequence by, for example, incorporating the nucleotide sequence encoding the target heterologous protein into the same expression vector into which the nucleotide sequence of the VFF2 polynucleotide sequence has been incorporated, under the control of a different promoter (FIG. 1A). Alternatively, the host cell can be transformed with two vectors, the first containing the polynucleotide encoding the Vff2 protein and the second containing the polynucleotide sequence encoding the target protein (FIG. 1B).

To achieve secretion of the target protein from the yeast host cells in the method of the present invention, a signal recognition sequence, or signal peptide, is incorporated at the 5N end of the target protein sequence in the expression vector. Suitable signal sequences can be chosen from among a number of sequences known to those of skill in the art and include, for example, the signal sequence from secreted invertase (SUC2), secreted acid phosphatase (PHO5), or yeast mating factor alpha.

When sec18 mutants are shifted from the permissive temperature of 20° C. to the restrictive temperature of about 37° C., the secretory pathway has been shown to be blocked between the endoplasmic reticulum and Golgi elements, and also at the plasma membrane. (Morin-Ganet, M. N., *Anat. Rec.* (1998) 251(2): 256–264.) When sec18 mutants are transformed with an expression construct containing the VFF2 polynucleotide sequence, as in the method of the present invention, however, the blockage in the secretory pathway is not observed. In fact, overexpression of the Vff2 protein in secretory mutants, such as the sec18-1 mutant, gives a higher rate of cellular protein secretion and an increase in cellular biomass (i.e., more cells per volume of media) that is at least about 2×higher than that of wild type strains. Furthermore, not only is the mutant rescued at the restrictive temperature, but also the strain grows several times faster than the wild type strain under the same growth conditions (FIG. 2). This control of growth by temperature can also be used according to the invention to select transformed cells without the need to incorporate an additional phenotype solely for the purpose of selection.

The present invention also provides a genetically altered cell such as a sec 18-1 mutant altered to express or overexpress the Vff2 protein, with increased capacity for heterologous protein secretion. Schweden, et al. (U.S. Pat. No. 5,672,487, the disclosure of which is incorporated herein by reference) describe a process for recombinant production of proteins in yeast, using the leader sequence of an animal peptide neurohormone to direct secretion of the recombinant protein. Hitzeman, et al. (U.S. Pat. No. 4,775,622, the disclosure of which is incorporated herein by reference) also describe the expression, processing and secretion of heterologous protein by yeast. Using leader sequences derived from the secretion signal sequences of mammalian interferon genes, they produced a heterologous protein product that was successfully secreted into the growth medium. Hinnen, et al. (U.S. Pat. No. 5,436,136, the disclosure of which is incorporated herein by reference) also describe upstream activation sites from the yeast PHO5 gene that provide inducible promoters in yeast expression systems. Techniques for producing heterologous proteins in yeast cell expression systems are therefore known to those of skill in the art, and a variety of techniques and genetic elements can be successfully employed for heterologous protein expression. The protein, polynucleotide sequence, and method of the present invention provide means for increasing protein production and secretion in any of these systems.

Increasing Protein Secretion in Large-Scale Fermentation

In batch fermentation processes, the sterile growth medium is inoculated with an appropriate yeast strain and the fermentation is carried out without additional growth medium. In the method of the present invention, the inoculum is provided as a subculture of yeast cells genetically altered to express the VFF2 polynucleotide sequence in conjunction with a target heterologous protein. The yeast cells can be, for example, yeast species such as *Saccharomyces cerevisiae, Schizosaccharomyces pombe, Yarrowia lipolytica, Pichia pastoris, Hansenula polymorpha*, or *Kluyveromyces lactis*. Cells should be chosen from secretory mutants of the species. A good secretory mutant for use in conjunction with VFF2 overexpression is the *Saccharomyces cerevisiae* sec18-1 mutant.

Cells are cultured through the stationary growth phase, and then harvested. When a secreted protein is the target protein, the protein can be isolated from the culture medium, as yeast generally secretes few proteins. Where the target protein is not secreted, a higher internal concentration is expected due to the increased protein production and translation machinery produced as a result of over-expression of VFF2.

A particular advantage of the claimed sequence and method of the present invention is the use of a secretory mutant cell over-expressing VFF2 in continuous fermentation. The cost of producing a specific amount of biomass is potentially much lower using continuous fermentation rather than batch fermentation. Continuous fermentations can be performed in smaller bioreactors than are batch fermentations, medium can be removed in smaller aliquots over time, making protein purification easier without requiring large-scale purification equipment and techniques, and continuous fermentations can be performed without the usual interruptions in fermentation processes that are characteristic of batch fermentations. Briefly, a subculture of yeast cell transformants expressing the VFF2 polynucleotide sequence is inoculated into a volume of appropriate medium. The yeast cell transformants can be chosen from among a number of yeast species, including, for example, *Saccharomyces cerevisiae, Schizosaccharomyces pombe, Yarrowia lipolytica, Pichia pastoris, Hansenula polymorpha*, or *Kluyveromyces lactis*. Cells should be chosen from secretory mutants of the species. A good secretory mutant for use in conjunction with VFF2 over-expression is the *Saccharomyces cerevisiae* sec18-1 mutant.

As the fermentation progresses over time, medium and cells are removed, and fresh medium is introduced into the fermentation vessel. The removed medium and cells can be separated by processes known to those of skill in the art, and the protein isolated from the appropriate fraction. Where the target protein is a secreted protein, the target protein can be isolated from the medium. Where the target protein is not a secreted protein, the target protein can be isolated from the cells, which have an increased intracellular protein concentration due to over-expression of the VFF2 polynucleotide sequence.

The secretion system can be used for recombinant target proteins that require either O-linked or N-linked glycosylation for biological activity. To facilitate protein secretion, an appropriate polynucleotide coding sequence for a signal peptide is functionally linked to the polynucleotide coding sequence of the target protein. The pre-pro-alpha-factor, or leader peptide coding sequence of the yeast mating type factor alpha1 gene is often cloned upstream of the target protein cDNA in order to route the protein for secretion. As the protein enters the secretory pathway and ultimately is exported from the cell, appropriate post-translational modifications are made, and the leader peptide is removed by an endogenous endoprotease that recognizes the dipeptide sequence Lys-Arg. Positioning the Lys-Arg sequence appropriately immediately upstream from the cDNA sequence insures that, following removal of the leader peptide, the target protein will have the appropriate amino acid residue at its N-terminus.

A number of recombinant target proteins have previously been expressed in *S. cerevisiae*, including the Hepatitis B virus surface antigen, the malaria circumsporozoite protein, the HIV-1 envelope protein, a variety of HIV-1 antigens and Hepatitis C proteins, human insulin, human epidermal growth factor, insulin-like growth factor, platelet-derived growth factor, proinsulin, alpha-I antitrypsin, factor XIIIa (for blood coagulation), and granulocyte-macrophage colony-stimulating factor.

These and other proteins can be produced at higher levels, and more easily purified, using the method of the present invention, in conjunction with standard cell culture and protein purification methods known to those of skill in the art.

Increased Production of Enzymatic Biocatalysts

Biotechnology provides a powerful technology for producing cleaner industrial processes and products. It is well known that enzymes provide valuable catalysts for a growing number of industrial processes. Biocatalytic enzymes provide the catalytic activity while minimizing waste generation and the number of process steps.

A significant example of the use of microorganisms, particularly yeast, as biocatalysts is provided by Gavagan, et al. (*J Org Chem.* (1997) 62: 549). The process, developed by the DuPont Company, produces glyoxylic acid from glycolic acid using a cellular transformant expressing an enzymatic catalyst derived from spinach and yeast. In U.S. Pat. No. 5,834,262 (incorporated herein by reference), Anton et al. describe a related process using the enzyme glycolate oxidase in the form of a microbial cell transformant that intracellularly expresses and retains in the cytoplasm or peroxisomes glycolate oxidase selected from the group consisting of transformants of *Aspergillus nidulans, Hansenula polymorpha, Pichia pastoris*, and *Escherichia coli*, under conditions where the transformants are permeabilized to the passage of carboxylic acids.

The sequence and method of the present invention provide increased secretion of biocatalytic molecules, such as the enzymes glycolate oxidase or catalase, for example.

Fernanedez-Lafuente et al. (Tetrahedron Letters (1997) 38: 4693) described the synthesis of a second-generation cephalosporin, Cefalozin, from cephalosporin C. The method of synthesis involved using three consecutive biotransformations catalyzed by D-aminoacid oxidase, glutaryl acylase and penicillin acylase. Although conventional synthesis involved toxic reagents for chemical activation of the acyl donor carboxylic groups, as well as the use of chlorinated solvents, the biocatalytic process allowed synthesis in one reaction vessel, did not involve toxic reagents or products, and reduced the steps needed to purify the protein.

High-Throughput Screening Using VFF2 Secretion Method

The sequence and method of the present invention also provide an improved method for high-throughput screening of compounds using yeast expression systems. High-throughput screening methods are known to those of skill in the art, and may rely upon various detection techniques, such as chemiluminescence, fluorescence, morphological, and absorbance assays. Chemiluminescent assays often use the bioluminescent substrate for luciferase, luciferin. The calcium ion-sensitive photoprotein aequorin is also used in chemiluminescent assays. Fluorescence assays are divided into at least three major categories: (1) intensity-based assays, in which the prototypic intensity-based indicator is Fluo-3, a fluorescein-based intracellular calcium ion sensor that increases its fluorescence intensity by about 100× when calcium is bound; (2) fluorescence resonance energy transfer (FRET), which results when two fluorophores (donor and acceptor) come in close proximity (excitation energy is transferred form the donor to the acceptor, decreasing donor intensity and increasing acceptor intensity), and (3) fluorescence localization or redistribution, which relies on the molecular translocation apparatus associated with cellular signaling. Examples of FRET probes include CCF2 (a beta-lactamase) and coulipids and oxonols. The most common probes for fluorescence localization or redistribution are chimeric green fluorescent proteins (GFPs).

Yeast-based high-throughput screens take advantage of the fact that yeasts grow rapidly, are easy and economical to culture, and can be easily genetically manipulated. G-protein coupled receptors (GPCRs), for example, have been successfully expressed in yeasts, as have proteins such as the human beta2-adrenergic receptor (expressed in *S. cerevisiae* under the control of the GAL1 promoter), a modified human beta2-adrenergic receptor (expressed in *S. pombe*), a human M1 muscarinic receptor, rat M5 muscarinic acetylcholine receptor, and a modified form of the mouse 5HT5a serotonin receptor (all expressed in *S. cerevisiae*). The native human dopamine D2s receptor has been expressed in both *S. cerevisiae* and *S. pombe*. In addition to the G-protein coupled receptors, yeasts have been used to express functional ion channels, mammalian peptide hormones, extracellular hormone ligand-binding proteins, and protein tyrosine kinases.

Given the wide variety of proteins that can be expressed, either as intracellular proteins or as secreted proteins, the method of the present invention provides an enhancement of high-throughput screening methods, allowing for greater ease of detection due to increased protein concentrations per well. High-throughput screening is performed, for example, in 96-well microtiter plates or in microtiter plates containing more than 96 wells. The quantity of cells cultured therein is therefore smaller than in larger culture vessels. A significant improvement in intracellular protein concentration, or in protein secretion, as provided by the sequence and method of the present invention, allows detection of reactive compounds with a smaller cell culture. Thus the sequence and method of the present invention facilitates high-throughput screening by increasing the concentration of target proteins in the screening samples.

The *S. cerevisiae* Sec18-1 VFF2 Strain of the Present Invention Can Be Used in Protein Expression Systems, in Biocatalysis, or in High-Throughput Screening The sec18-1 VFF2 *S. cerevisiae* strain of the present invention was produced by transforming a sec18-1 temperature-sensitive strain with a yeast centromeric plasmid that contains the VFF2 gene behind the GAL1 promoter. This plasmid also contained the URA3 selectable marker so that transformants could be selected on minimal media lacking uracil.

The resulting cells exhibit greater cellular biomass and increased protein secretion relative to wild type *S. cerevisiae* strains for a given amount of time. These cells can be transformed with appropriate expression vectors containing any of a number of foreign polynucleotide sequences, such as a target protein that may be toxic internally to a cell, but is not if secreted externally. Such secreted proteins can then be harvested from the media.

The cells can also be transformed with appropriate expression vectors containing the polynucleotide sequence of a catalytic enzyme to produce a biocatalyst, secreting the enzyme at a rate higher than that obtained from wild type cells. Furthermore, the cells are ideal for high-throughput screening of a variety of compounds that interact with, for example, G-protein coupled receptors, hormones, and protein tyrosine kinases.

EXAMPLES

Example 1

Genetic Screen

The purpose of this genetic screen was to identify potential genes that genetically interact with or can compensate for the loss of the SEC17gene in the budding yeast, *Saccharomyces cerevisiae*. The Sec17 protein is a yeast homolog of the mammalian protein alpha-SNAP that is involved in the process of membrane fusion and secretion in the cell.

A temperature-sensitive (ts) sec17-1 strain was transformed with an overexpression *S. cerevisiae* cDNA library. This library consisted of plasmids with a selectable auxotrophy marker and a cDNA fragment behind a galactose-inducible promoter sequence. The colonies obtained from the transformation were replica plated and placed at 37° C., the non-permissive temperature for the sec17-1 strain. Colonies that subsequently grew at 37° C. were selected and the plasmid they harbored was isolated. This plasmid was re-transformed into the same strain to confirm the suppression of the sec17-1 temperature sensitive phenotype. The plasmid was then transformed into *E. coli* for plasmid mini-preps. One such plasmid was later identified to contain a novel ORF, which was named VFF2.

Example 2

Sequence Identification

A mini-prep of the plasmid was sent along with standard T3/T7 sequencing primers, was sequenced at the in-house sequencing facility at the Salk Institute.

The sequence was then placed in a search in the *Saccharomyces* Genome Database and was identified as the ORF YDR361c, consisting of 852 base pairs encoding a protein of 283 amino acids. From the predicted protein structure, the full length protein should be around 32 kDa.

A BLAST search for homologies with other gene sequences entered into the NCBI GenBank did not turn up any significant homology with other known genes. A BLAST search for homologies with other protein sequences turned up *Schizosaccharomyces pombe*, *Arabidopsis thaliana*, and *Caenorhabditis elegans* hypothetical proteins that are 56–40% homologous.

Example 3

Characterization of VFF2

A. Suppression of Other Secretory Mutations by VFF2

The purpose of the present experiment was to determine if the overexpression of VFF2 could suppress the temperature sensitive phenotype of other secretory (sec) mutant strains.

The original overexpression plasmid isolated from the genetic screen that contained VFF2 was transformed it into other sec mutants. A control plasmid was also constructed in which the VFF2 cDNA was cut out and the vector was closed by religating. This was done to ensure that the suppression phenotype was correlated with the presence of the VFF2 polynucleotide sequence and not just an effect of the vector or the GAL promoter. Once the sec mutant strains that contained these plasmids was obtained, the strains were struck on plates containing galactose, allowed to grow at the permissive temperature for 6–12 hours, and then shifted to the non-permissive temperature of 37° C. for 48 hours. As a negative control, a strain that has a temperature sensitive mutation in topoisomerase II, a DNA replication enzyme, but should otherwise exhibit normal secretory processes, was transformed.

Overexpression of VFF2 can suppress the ts phenotype of a variety of sec mutants including sec18-1 (the yeast homolog of mammalian NSF, an ATPase involved in membrane fusion), bet1-1 and sec22-2 (two t-SNARE molecules involved in ER-to-Golgi fusion, and cdc48-2 (and ATPase similar to NSF that participates in ER—ER homotypic fusion). Overexpression of VFF2 did not suppress the topoisomerase mutation and did not suppress ufe1-1 (a t-SNARE involved in ER—ER fusion and retrograde or Golgi-to-ER traffic). No effect was seen in any strain containing only the control plasmid.

VFF2 can suppress a variety of secretory mutations in the ER-to-Golgi pathway but not in the retrograde, Golgi-to-ER pathway. Furthermore, VFF2 is a strong suppressor of the sec18-1 mutation that has never been found to be suppressed by any other polynucleotide sequence before.

B. Depletion Experiments

Depletion experiments were performed to determine how much Vff2 protein is needed to rescue a VFF2 knockout strain.

A VFF2 heterozygous diploid (VFF2 is deleted on one copy of the genome) strain was obtained from Research Genetics. A knockout of YDR361c was requested. The deletion of this gene is lethal, which was confirmed by sporulating the diploid and dissecting tetrads, of which only the two that still had the intact VFF2 polynucleotide sequence were viable. The diploid strain was transformed with the above-described VFF2 overexpression plasmid and sporulated. Tetrads were dissected on plates containing galactose to induce overexpression of the plasmid copy of VFF2. Spores were then selected that had the genomic copy of VFF2 deleted and harbored the plasmid were selected. The colonies that grew up from these spores were then streaked onto plates containing 2%, 1.5%, 1%, 0.5%, and 0% galactose.

There was no detectable difference in growth between 2% and 0.5% galactose plates and all of the strains tested grew robustly. The strains grew more weakly on the plates that contained 0% galactose.

Because the GAL promoter that was used is known to be a somewhat "leaky" system, it is likely that even in the absence of galactose, a few copies of VFF2 are being expressed from the plasmid. Growth on 0% galactose plates is then interpreted to mean that even a few copies of the Vff2 protein are sufficient to rescue a cell that lacks a genomic copy of VFF2.

C. Cellular Localization of Vff2 Protein

Experiments were also performed to determine the cellular localization of the Vff2 protein.

A green fluorescent protein (GFP)-Vff2 fusion protein was made by placing VFF2 behind the GFP polynucleotide sequence on a yeast expression vector including a galactose-inducible promoter. This plasmid was transformed into a wild type yeast strain. This strain was then grown in media containing 2% galactose to induce expression of the GFP-Vff2 protein. The live cells were visualized on a deconvolution microscope.

The fusion protein localized predominantly to the nuclei of the cells. It is unclear whether staining in the cytoplasm is localized to membranous structures or is diffuse throughout the cell.

D. Growth Curves for Strains Overexpressing VFF2

It was observed during the suppression experiments that certain strains overexpressing VFF2 seemed to grow better on plates than their original parent strain even at permissive temperature. In fact, even the wild type strain overexpressing VFF2 outgrew the wild type strain without the VFF2 plasmid. This observation led to the hypothesis that if overexpression of VFF2 leads to increased cell growth, it must also increase secretion of the plasma membrane and the proteins that make up the cell wall, as this is necessary for growth and division of yeast cells. In order to assess the levels to which growth was increased in these cells, growth curve experiments were performed.

Figure 3A:
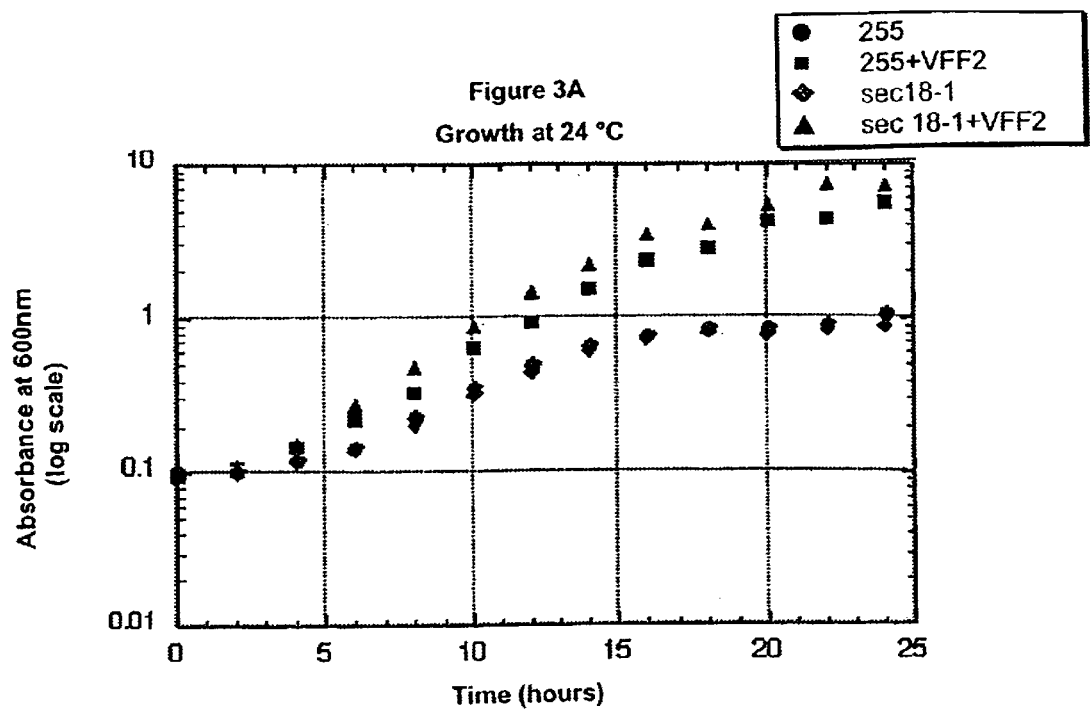
FIGS. 3A and 3B. These figures depict growth curves for various yeast strains.
Figure 3B:
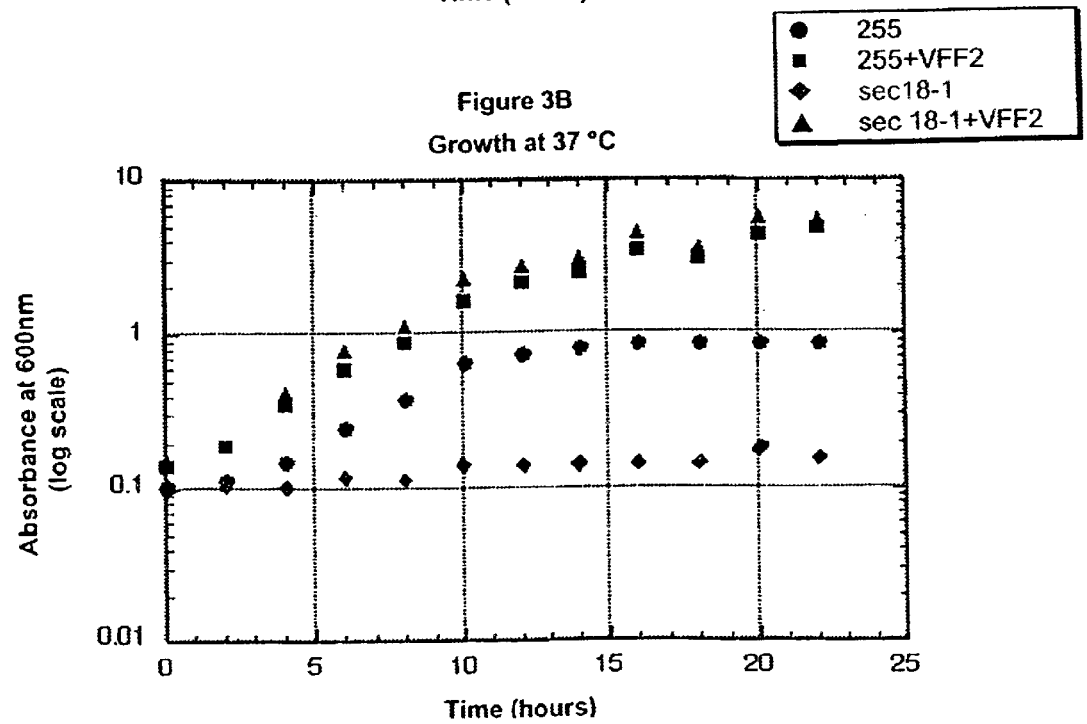

Growth curves were generated for four different strains: RSY255 (a wild type strain with a similar genetic background to most of the sec mutants used in the above experiments), RSY255+VFF2, sec18-1, and sec18-1+VFF2 (FIGS. 3A and 3B). Each strain was grown in liquid media containing 2% galactose overnight at the permissive temperature. The next day, each strain was reset to a density of $3 \times 10^6$ cells/mL and then every two hours an optical density (O.D.) reading was taken for 22 hours. In another set of experiments, the cultures were shifted to the non-permissive temperature of 37° C. after being reset to $3 \times 10^6$ cells/mL.

For the experiment carried out at 24° C., the RSY255 and sec18-1 strains grew in a logarithmic fashion and at the end of 22 hours had reached a plateau around 2.7×cells/mL. The RSY255+VFF2 and the sec18-1+VFF2 strains grew much more rapidly and after only 6 hours were 1.5-fold and 2-fold denser than the RSY255 and sec18-1 cultures, respectively. At the end of 22 hours, the RSY255+VFF2 culture had reached a density of $1.3 \times 10^8$ cells/mL and the sec18-1+VFF2 culture had reached a density of $2.2 \times 10^8$ cells/mL. This represents a 5-fold difference in growth between the RSY255 strain and the RSY255+VFF2 strain and an 8-fold difference in growth between the sec18-1 strain and the sec18-1+VFF2 strain.

For the experiment carried out at 37° C., the sec18-1 strain arrested growth at around $4.5 \times 10^6$ cells/mL that was expected for this strictly ts strain. RSY255 grew similarly at 37° C. and 24° C., giving a logarithmic curve that reached a plateau at 22 hours of $2.6 \times 10^7$ cells/mL. The RSY255+VFF2 and the sec18-1+VFF2 strains reached densities of 1.5 and $1.7 \times 10^8$ cells/mL, respectively at 22 hours. This represents a 5.7-fold difference in growth between RSY255 and RSY255+VFF2 and a 38-fold difference in growth between the sec18-1 and the sec18-1+VFF2 strains.

The overexpression of VFF2 is correlated with an increased growth phenotype of both a wild type strain and the sec mutant strain sec18-1. The increased growth is observed at both the 24° C. permissive temperature and the 37° C. non-permissive temperature. One striking observation is that at both temperatures, the strains overexpressing VFF2 show no signs of a plateau in their growth curves after 22 hours. In order for these strains to be growing so rapidly, they must be secreting plasma membrane and cell wall components at a higher rate. Any protein that contains a signal peptide that targets it to be secreted outside of the cell will also be secreted at a higher rate. These proteins are carried inside the membrane vesicle that fuses with the plasma membrane to add more membrane to the growing cell and therefore their secretion is tied to cell growth. By pulse-labeling cells and then precipitating any proteins that have been secreted into the media, a secretion profile of the strains overexpressing VFF2 and the original parent strains can be generated.

The invention is described with reference to various specific and preferred embodiments and techniques. It should be understood, however, that many variations and modifications may be made while remaining within the scope of the invention. All referenced publications, patents, and patent documents are intended to be incorporated by reference, as though individually incorporated by reference.

REFERENCES

1. Zsebo KM, Lu HS, Fieschko JC, Goldstein L, Davis J, Duker K, Suggs SV, Lai PH, Bitter GA, *J. Biol. Chem.* 1986 May 5; 261(13):5858–65. Protein secretion from *Saccharomyces cerevisiae* directed by the prepro-alpha-factor leader region.
2. Witt W, Mertsching A, Konig E, *Biochim Biophys Acta* 1984 Aug. 15; 795(1):117–24. Secretion of phospholipase B from *Saccharomyces cerevisiae.*
3. Brake AJ, Merryweather JP, Coit DG, Heberlein UA, Masiarz FR, Mullenbach GT, Urdea MS, Valenzuela P, Barr PJ, *Proc Natl Acad Sci USA* 1984 August; 81(15):4642–6. Alpha-factor-directed synthesis and secretion of mature foreign proteins in *Saccharomyces cerevisiae.*

What is claimed is:

1. An isolated polynucleotide comprising a sequence encoding a vesicular fusion factor 2 protein (Vff2p), comprising SEQ ID NO:2, and further comprising a sequence encoding a heterologous target protein.

2. The polynucleotide of claim 1, further comprising SEQ ID NO:1.

3. The polynucleotide of claim 1, wherein the encoded Vff2p is about 32 kD.

4. The polynucleotide of claim 1, further comprising a promoter operatively linked to the sequence encoding the Vff2p.

5. The polynucleotide of claim 4, further comprising a second promoter operably linked to the sequence encoding the target protein.

6. The polynucleotide of claim 5, wherein the second promoter is a promoter that functions in the host cell to direct transcription of the target protein.

7. The polynucleotide of claim 4 wherein the promoter is a promoter that functions in a host cell to direct transcription of the sequence encoding the Vff2p.

8. The polynucleotide of claim 7, wherein the host cell is a yeast cell.

9. The polynucleotide of claim 8, wherein the yeast cell is a *Saccharomyces cerevisiae, Schizosaccharomyces pombe, Yarrowia lipolytica, Pichia pastoris, Hansenula polymorpha*, or *Kluyveromyces lactis*.

10. An isolated polynucleotide comprising a sequence encoding a vesicular fusion factor 2 protein comprising SEQ ID NO:2, and further comprising a sequence encoding a heterologous target protein, wherein the vesicular fusion factor 2 protein increases *Saccharomyces cerevisiae* cell growth or protein secretion.

11. An isolated polynucleotide comprising SEQ ID NO:1 encoding a vesicular fusion factor 2 protein that increases *Saccharomyces cereviae* cell growth or protein secretion, and further comprising a sequence encoding a heterologous target protein.

12. A polynucleotide expression vector comprising a polynucleotide encoding a Vff2p comprising SEQ ID NO:2.

13. The expression vector of claim 12, wherein the encoded protein is about 32 kD.

14. The expression vector of claim 12, further comprising a sequence encoding a heterologous target protein.

15. The expression vector of claim 14, wherein transcription of the target protein is directed by a second promoter.

16. The expression vector of claim 15, wherein the second promoter is a promoter that functions in the host cell to direct transcription of the target protein.

17. The expression vector of claim 12, further comprising a promoter sequence operatively linked to the sequence encoding the Vff2p.

18. The expression vector of claim 17 wherein the promoter is a promoter that functions in a host cell to direct transcription of the sequence encoding the Vff2p.

19. The expression vector of claim 18, wherein the host cell is a yeast cell.

20. The expression vector of claim 19, wherein the yeast is *Saccharomyces cerevisiae, Schizosaccharomyces pombe, Yarrowia lipolytica, Pichia pastoris, Hansenula polymorpha*, or *Kluyveromyces lactis*.

21. An expression vector comprising SEQ ID NO:1, or a sequence encoding SEQ ID NO:2.

22. A polynucleotide expression vector comprising a polynucleotide encoding a vesicular fusion factor 2 protein comprising SEQ ID NO:2, wherein the vesicular fusion factor 2 protein increases *Saccharomyces cerevisiae* cell growth or protein secretion.

23. A composition comprising two vectors, the first vector comprising a polynucleotide encoding the vesicular fusion factor 2 protein and the second vector comprising a polynucleotide encoding a heterologous target protein.

24. The composition of claim 23, wherein the polynucleotide encoding the heterologous target protein further comprises a signal sequence.

25. A recombinant host cell comprising a yeast cell genetically altered to express a protein encoded by a polynucleotide sequence encoding a functional Vff2p, wherein the Vff2p comprises SEQ ID NO:2.

26. The recombinant host cell of claim 25, wherein said polynucleotide sequence comprises SEQ ID NO:1.

27. The host cell of claim 25, further comprising a sequence encoding a heterologous target protein.

28. The host cell of claim 25, wherein the yeast cell is a *Saccharomyces cerevisiae, Schizosaccharomyces pombe, Yarrowia lipolytica, Pichia pastoris, Hansenula polymorpha*, or *Kluyveromyces lactis* cell.

29. The host cell of claim 25, wherein the host cell lacks a functional protein involved in the secretory pathway and/or involved in the required cellular machinery for membrane fusion, other than Vff2p.

30. A recombinant host cell comprising a *Saccharomyces cerevisiae* cell genetically altered to express a protein encoded by a polynucleotide sequence encoding a vesicular fusion factor 2 protein comprising SEQ ID NO:2.

31. An isolated vesicular fusion factor 2 protein comprising SEQ ID NO:2, and further comprising a heterologous target protein.

32. A method for increasing cell growth of a yeast host cell, comprising introducing a polynucleotide sequence encoding Vff2p into the cell and culturing the cell, wherein the Vff2p comprises SEQ ID NO:2 whereby cell growth of the yeast host cell is increased.

33. The method for increasing cell growth of a cell according to claim 32, wherein the host cell is cultured under conditions effective to allow expression of the Vff2p.

34. A method for increasing cell growth of a *Saccharomyces cerevisiae* host cell, comprising introducing a polynucleotide sequence encoding a vesicular fusion factor 2 protein comprising SEQ ID NO:2 into the cell and culturing the cell, whereby cell growth of the *Saccharomyces cerevisiae* host cell is increased.

35. A method for increasing protein secretion from a yeast host cell, comprising introducing a polynucleotide sequence encoding Vff2p into the cell and culturing the cell, wherein the Vff2p comprises SEQ ID NO:2 whereby protein secretion from the yeast host cell is increased.

36. The method for increasing protein secretion from a cell according to claim 35, wherein the host cell is cultured under conditions effective to allow expression of the Vff2p.

37. A method for increasing protein secretion from a yeast host cell, comprising introducing a polynucleotide sequence encoding a vesicular fusion factor 2 protein comprising SEQ ID NO:2 into the cell and culturing the cell, whereby protein secretion of the yeast host cell is increased.

38. A method of selecting for a yeast secretory mutant cell containing a polynucleotide sequence encoding a Vff2p operably linked to a promoter, wherein the Vff2p comprises SEQ ID NO:2, the method comprising growing the yeast secretory mutant cell at a restrictive temperature of about 32–37° C., wherein the restrictive temperature selectively favors mutant cell growth, thereby selecting for a yeast secretory mutant cell containing a polynucleotide sequence encoding a Vff2p operably linked to a promoter.

39. The method of claim 38, wherein the temperature is at about 37° C.

40. The method of claim 38, wherein the polynucleotide further comprises a sequence encoding a heterologous target protein operably linked to a second promoter.

41. The method of claim 32, 35 or 38, wherein the yeast cell is a *Saccharomyces cerevisiae, Schizosaccharomyces pombe, Yarrowia lipolytica, Pichia pastoris, Hansenula polymorpha*, or *Kluyveromyces lactis* cell.

42. The method of claim 38, wherein the secretory mutant cell is sec17-1, sec 18-1, bet1-1, sec22-2, uso1-1, pex3-1, sed5-1, cdc48-2, sec7-5, or ypt1-3.28.

43. The method of claim 42, wherein the secretory mutant cell is sec17-1, sec18-1, bet1-1, sec22-2, uso1-1, or pex3-1.

44. The method of claim 43, wherein the secretory mutant cell is sec18-1.

* * * * *